US00PP09194P

United States Patent [19]

Dehan

[11] Patent Number: Plant 9,194

[45] Date of Patent: Jul. 11, 1995

[54] IMPATIENS PLANT NAMED 'PINKY GINI'

[75] Inventor: Klara Dehan, Holon, Israel

[73] Assignee: Danzinger "Dan" Flower Farm, Hashiva, Israel

[21] Appl. No.: 299,613

[22] Filed: Sep. 2, 1994

[51] Int. Cl.[6] ..... A01H 5/00
[52] U.S. Cl. ..... Plt./87.6
[58] Field of Search ..... Plt. 87.6

*Primary Examiner*—James R. Feyrer
*Attorney, Agent, or Firm*—Foley & Lardner

[57] ABSTRACT

A new and distinct cultivar of impatiens plant named Pinky Gini, characterized by its very small dark green leaves and small flowers, with the flowers standing well above the leaves, red-purple flower color with a white center eye; excellent self-branching and compact growth habit, and its very early flowering.

1 Drawing Sheet

The present invention relates to a new and distinctive cultivar of impatiens plant, botanically known as Impatiens, commercially known as New Guinea Impatiens, and known by the cultivar name Pinky Gini.

The new cultivar was developed by the inventor Klara Dehan in Mishmar Hashiva, Israel in a controlled breeding program. The female or seed parent was a cultivar identified by the breeding number 80 PR, and the male or pollen parent was a cultivar identified by the breeding number 72 LR. Both parents are proprietary cultivars used in the breeding program. The new cultivar was selected by the inventor from the progeny of the stated cross.

Asexual reproduction of the new cultivar by leaf cuttings by the inventor in Mishmar Hashiva, Israel has established that the unique features of this new impatiens are stabilized and are reproduced true to type by successive propagations.

The following characteristics in combination distinguish the new impatiens Pinki Gini from both its parent varieties and other cultivated Impatiens of this type known and used in the floriculture industry:

1. The primary distinguishing features are the relatively small flowers and the small leaves, with the flowers standing well above the leaves.
2. The flowers are red-purple with a white center eye.
3. The small leaves are dark green in color.
4. Excellent self-branching.
5. The cultivar is particularly suitable for small pots 7–10 cm in diameter.
6. The cultivar can be propagated by leaf cuttings year around.
7. Very early flowering.

The accompanying color photographic drawing illustrates the overall appearance of the cultivar, with the colors being as true as it is reasonably possible to obtain in a colored reproduction of this type. The flower color of the new cultivar is not accurately illustrated, with the actual color being more purple and less red. The color values described below are accurate.

The following is a detailed description of the new impatiens cultivar based on plants produced under commercial practice in Mishmar Hashiva, Israel. The plants described were grown in a net-covered greenhouse during the summer season with temperatures ranging from 35° C. maximum to 18° C. minimum. Color references are made to the Royal Horticultural Society Colour chart except where general terms of ordinary dictionary significance are used.

Parentage: The female parent 80 PR and the male parent 72 LR are seedlings from breeding program.

Propagation:

*Type cutting.*—Leaf cuttings.

*Time to initiate roots.*—7–8 days at 25° C. in summer; 8–9 days at 20° C. in winter.

*Rooting habit.*—Roots well.

Plant description:

*Form.*—Excellent self-branching produces a full, rounded symmetrical plant.

*Habit of growth.*—Compact growth habit; the plant is particularly suited to small pots 7–10 cm in diameter.

*Foliage.*—Size: Small; mature leaves 5.0 cm long and 2.0 cm wide. Shape: Lanceolate to ovate. Margin: Serrated. Color: Young and mature foliage, top side 147A; under side 147B. Venation: Light green.

Flowering description:

*Flowering habits.*—Flowering is very early. The initiation of flower buds takes about 5 weeks from potting leaf cutting. Flowers are completely open approximately 7 weeks after potting.

*Natural flowering season.*—The new cultivar flowers under ambient conditions in Israel all year, but in the winter season with less light, there are fewer flowers.

*Flower buds.*—Buds before opening are small, approximately 1.0 cm in length and 0.8 cm in width. Length of spur is 2.5 cm, and length of pedicel is 2.5 cm.

*Flowers borne.*—Flowers fully open from initiation in about 2 weeks; flowering continues all season.

*Quantity of flowers.*—Very floriferous; 20–25 flowers are open at the same time, with continuous flowering.

*Petals.*—Two (2) pairs of heart-shaped petals and a single larger petal; petals overlap. Color: Top side when opening 72B-C, fading slightly to 74B; white center eye; under side 72C; Number of petals: Five (5). Size of Flowers: Small; approximately 4 cm in diameter.

*Reproductive organs.*—Stamens: One (1) in number. Anthers: Round, color light red. Pollen color:

White. Pistils: Stigma: Round in shape, nearly white in color. Ovaries: Four (4) in number, 1 mm in size; light green in color.

Disease resistance: No significant disease problem noted to date.

I claim:

1. A new and distinct cultivar of Impatiens plant named Pinky Gini, as illustrated and described.

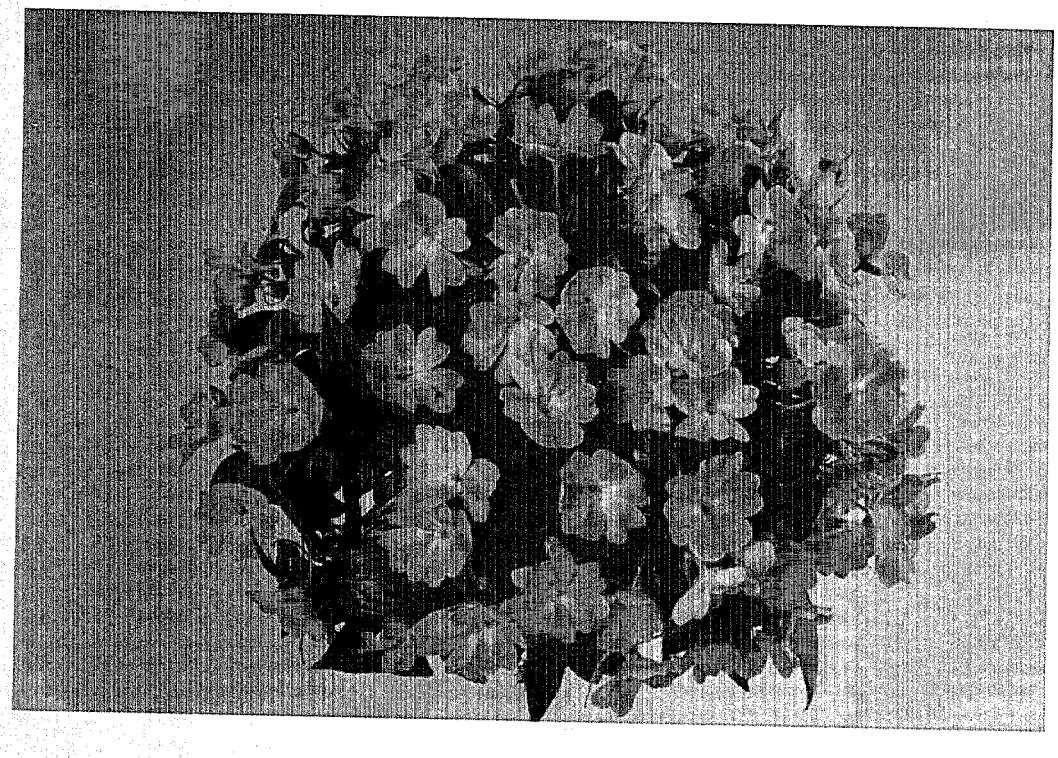

* * * * *